United States Patent [19] [11] Patent Number: 4,688,087
Ams et al. [45] Date of Patent: Aug. 18, 1987

[54] LIGHT PROJECTOR HAVING A CONTROLLABLE INTENSITY OF ILLUMINATION

[75] Inventors: Felix Ams, Kämpfelbach; Ulrich Bolg, Sulzfeld; Helmut Wurster, Oberderdingen, all of Fed. Rep. of Germany

[73] Assignee: Richard Wolf GmbH, Fed. Rep. of Germany

[21] Appl. No.: 829,615

[22] Filed: Feb. 14, 1986

[30] Foreign Application Priority Data

Mar. 19, 1985 [DE] Fed. Rep. of Germany ....... 3509825

[51] Int. Cl.$^4$ .............................................. H04N 7/18
[52] U.S. Cl. ..................................... 358/100; 358/98; 358/228
[58] Field of Search ................. 358/98, 100, 228, 161, 358/162, 168, 99, 211; 128/6; 354/225, 226, 227.1, 241, 246, 247

[56] References Cited

U.S. PATENT DOCUMENTS

| 4,202,014 | 5/1980 | Gilligan et al. | 358/228 |
| 4,423,436 | 12/1983 | Kimura | 358/98 |
| 4,489,350 | 12/1984 | Kimura | 358/228 X |
| 4,516,172 | 5/1985 | Miyata et al. | 358/228 |
| 4,584,610 | 4/1986 | Mizokami et al. | 358/228 |
| 4,599,654 | 7/1986 | Monroe | 358/228 |

Primary Examiner—Tommy P. Chin
Assistant Examiner—Victor R. Kostak
Attorney, Agent, or Firm—Hill, Van Santen, Steadman & Simpson

[57] ABSTRACT

The light projector provided with a system for setting the intensity of illumination for a cavity which is being filmed by means of a video camera, and from which the picture is shown on a monitor screen. The video signal from the camera is supplied as an actual value to a comparator which, as a function of the signal and of an adjustable reference value, drives a servo-motor connected to its output side, which adjusts the intensity of illumination within the cavity by means of a shutter situated in the beam path of the light projector.

6 Claims, 5 Drawing Figures

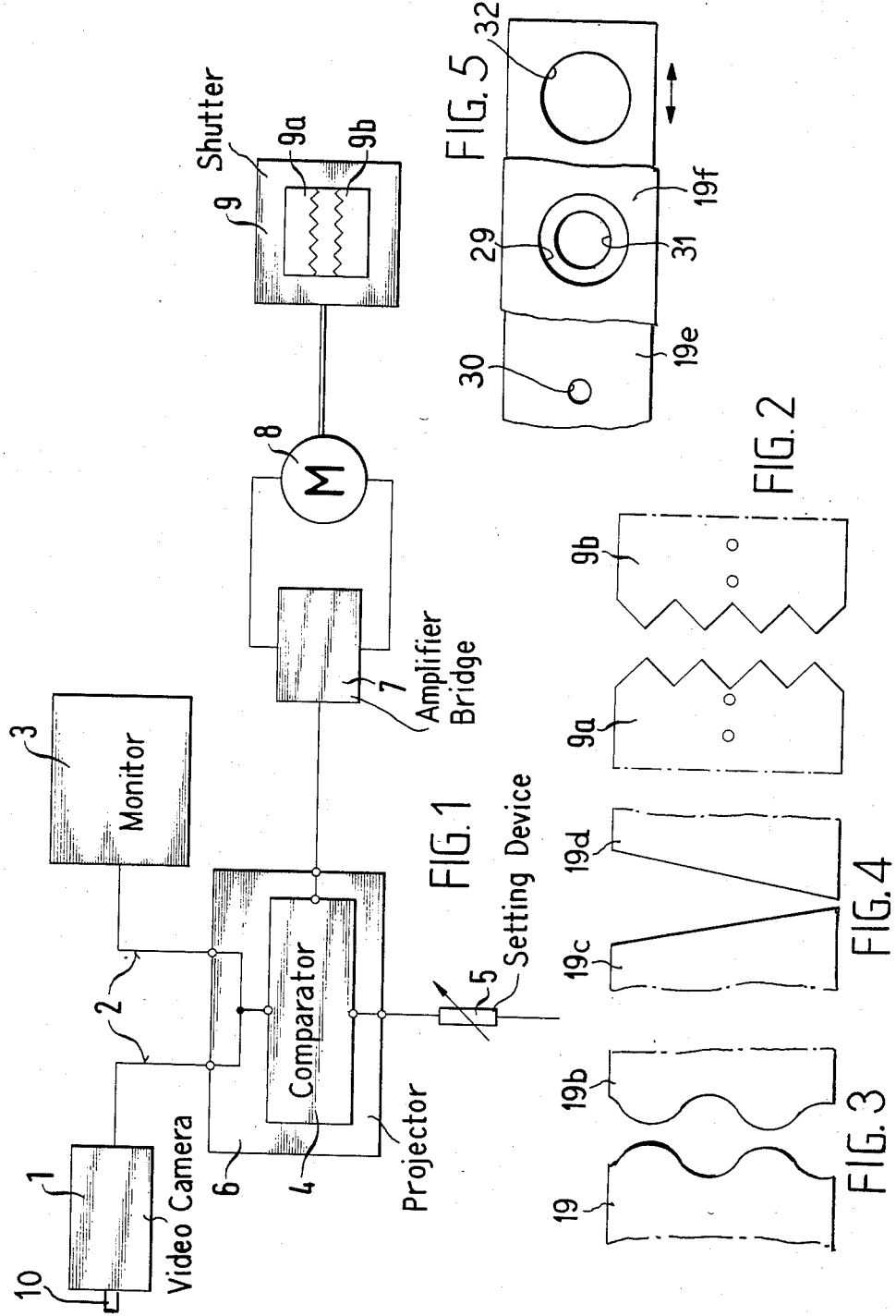

LIGHT PROJECTOR HAVING A CONTROLLABLE INTENSITY OF ILLUMINATION

BACKGROUND OF THE INVENTION

The invention relates to a light projector comprising a system for adjusting the intensity of illumination for human or animal bodily cavities or of hollow spaces in machinery or the like which are to be endoscopically examined and/or filmed by means of a video camera, the picture taken by the video camera being displayable on a monitor screen.

DESCRIPTION OF THE PRIOR ART

For the purpose of examining and above all of filming objects in bodily cavities or hollow technical spaces by means of an endoscope and of a video camera connected thereto, a light projector of high luminous output is required, which may be adjusted manually by the doctor to a fundamental brightness. The optimum brightness within the bodily cavity is thereby obtained within a limited range of the object distance from the endoscope extremity. At a greater distance of the object from the distal extremity of the endoscope, the quantity of light will no longer be sufficient for filming, whereas at too short a distance an excessive illumination occurs which may lead to a glare effect and to faulty exposure during filming.

SUMMARY OF THE INVENTION

It is an object of the invention to secure an automatic adjustment of the quantity of light as a function of the object spacing from the distal light outlet of an endoscope, whilst filming an object within a bodily cavity or a hollow technical space by means of a connected video camera with image reproduction by means of a monitor screen.

According to the invention, this object is achieved in that in a system of the type referred to in the foregoing, the video signal is supplied as an actual value to a comparator which, as a function of the video signal and an adjustable predetermined reference value, drives a servo-motor connected to its output side, which adjusts the intensity of illumination in the cavity by means of a shutter situated in the beam path of the light projector.

It is possible with this solution to secure correct adjustment of the illumination of the object at its distance from the distal light output from the endoscope utilised and to limit the same to its maximum amplitude, especially if the shutter has to be closed almost completely for light limitation, because of an excessive illumination of the object. In this connection, to prevent an excessive variation of brightness which has a deleterious effect on the electrical control operation, and an instability of the system as a whole because of the electro-mechanical time constant of the servo-motor, preferred embodiments of the invention include a regularly or irregularly curved extension of the mutually opposed edges of the shutter blades, their momentary overlap proportionally governing the intensity of illumination.

Further objects and advantages of the invention will become apparent from the following detailed description when read in conjunction with the accompanying drawings which illustrate a preferred embodiment of the invention.

BRIEF DESCRIPTION OF THE DRAWINGS

FIG. 1 shows a circuit diagram of a system for adjusting the illumination of an object as a function of the object spacing from the distal light outlet extremity of an endoscope, FIG. 2 shows a diagrammatical view of two blades forming a shutter, FIG. 3 shows a diagrammatical view of an embodiment of two blades forming the shutter, FIG. 4 shows a diagrammatical view of another embodiment of two blades forming the shutter, and FIG. 5 shows a diagrammatical view of yet another embodiment of the two blades forming the shutter.

DETAILED DESCRIPTION OF THE PREFERRED EMBODIMENT

Referring first to FIG. 1, a system for setting up the correct illumination of an object within a bodily cavity or a hollow technical space as a function of its distance from the distal light egress extremity of an endoscope comprises a video camera 1 connected to the proximal light conductor extremity 10 of an endoscope and the camera creates a video signal which is supplied via conductors 2 to a monitor 3 and simultaneously to a control unit 4 acting as a comparator. By means of a setting device 5 on the light projector 6, the comparator 4 may be set as a function of the actual value of the maximum permissible amplitude of the video-signal.

A comparison is made by the comparator 4 between the actual value of the video signal and the preset scheduled value, the output signal of the comparator 4 energizes—via an amplifier bridge 7—the servo-motor 8, which operates a shutter 9 comprising the two blades 9a, 9b movable towards and away from each other, and the servo-motor 8 closes or opens the shutter 9 to a greater or lesser extent as a function of the preset scheduled value.

To this end, to prevent excessive brightness changes, the mutually opposed edges of the shutter blades 9a, 9b are provided with a shape differing from the rectilinear, which in case of overlaps leads to gradually increasing or decreasing shutter apertures, thereby allowing for a gently intervening light quantity limitation.

The blade edges may have an undulant outlines or profiles of blades 19 and 19b (FIG. 3), toothed profiles or outlines of blades 9a and 9b (FIG. 2) or other outliner, and, the crests of the undulations or the teeth being mutually opposed. The edges of the two blades may also be allowed to extend rectilinearly as the blades 19c and 19d (FIG. 4) and their edges should however subtent a taper angle between them. Furthermore, one blade 19f (FIG. 5) of the mutually overlapping blades may be provided with a larger perforation 29 and the other blade 19e with smaller perforations 30, 31 and 32 which may be placed in congruence with the larger perforation 29. The two blades may be moved singly or in overlapped form into or out of the beam path of the light projector.

What is claimed is:

1. A light projector assembly comprising a system for adjusting the intensity of the illumination of a cavity to be examined by means of video camera, said assembly including a light projector having a beam path, a shutter with a shutter aperture being arranged in the light path and having two blades, which are movable towards each other to overlap for a closing action and in the opposite direction for an opening action, the shutter aperture being determined by the area of at least one gap between the mutually opposed blade edges, a video camera for creating a video signal in response to an image being illuminated in said cavity, a monitor screen for receiving the video signal and displaying the image recorded by the video camera, a comparator receiving the video signal as an actual value and comparing it to an adjustable predetermined reference value to create an output signal on an output, a servo-motor being connected to the output of the comparator and opening and closing the shutter aperture in response to the output signal of the comparator to vary the amount of light passing through the shutter aperture to the cavity.

2. A light projector as claimed in claim 1, wherein said reference value corresponds to the maximum permissible amplitude of the video signal.

3. A light projector as claimed in claim 1, wherein the blade edges have undulant profiles and the crests of the undulations of the two blade edges are aligned with each other.

4. A light projector as claimed in claim 1, wherein the blade edges have a toothed profile and the respective teeth of the two blades are aligned with each other.

5. A light projector as claimed in claim 1, wherein the edges of the blades extend at an angle to each other and form a wedge-shaped shutter aperture between them.

6. A light projector as claimed in claim 1, wherein the mutually overlapping blades movable with respect to each other are provided with perforations therethrough.

* * * * *